US011111200B2

(12) United States Patent
Shi et al.

(10) Patent No.: US 11,111,200 B2
(45) Date of Patent: Sep. 7, 2021

(54) METHOD FOR PREPARING ACRYLIC ACID AND METHYL ACRYLATE

(71) Applicant: Dalian Institute of Chemical Physics, Chinese Academy of Sciences, Dalian (CN)

(72) Inventors: Lei Shi, Dalian (CN); Zongmin Liu, Dalian (CN); Youming In, Dalian (CN); Wenliang Zhu, Dalian (CN); Yong Liu, Dalian (CN); Hongchao Liu, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 214 days.

(21) Appl. No.: 16/463,415

(22) PCT Filed: Nov. 25, 2016

(86) PCT No.: PCT/CN2016/107284
§ 371 (c)(1),
(2) Date: May 23, 2019

(87) PCT Pub. No.: WO2018/094691
PCT Pub. Date: May 31, 2018

(65) Prior Publication Data
US 2021/0114963 A1    Apr. 22, 2021

(51) Int. Cl.
*C07C 51/12* (2006.01)
*B01J 29/18* (2006.01)
(Continued)

(52) U.S. Cl.
CPC .............. *C07C 51/12* (2013.01); *B01J 29/18* (2013.01); *B01J 29/40* (2013.01); *B01J 29/65* (2013.01);
(Continued)

(58) Field of Classification Search
CPC ......... C07C 51/12; C07C 67/37; C07C 57/04; C07C 69/54; C07C 67/36; C07C 51/10;
(Continued)

(56) References Cited

U.S. PATENT DOCUMENTS

2010/0105947 A1* 4/2010 Celik ................. C07C 67/37
560/232
2014/0343319 A1* 11/2014 Goebel ................ C07C 51/353
562/599
2015/0343431 A1* 12/2015 Parvulescu .......... B01J 29/7057
562/599

FOREIGN PATENT DOCUMENTS

CN          104119228 A     10/2014

* cited by examiner

*Primary Examiner* — Brandon J Fetterolf
*Assistant Examiner* — Blaine G Doletski
(74) *Attorney, Agent, or Firm* — Edwin A. Sisson, Attorney at Law, LLC; Jeffrey J. Banyas

(57) ABSTRACT

The present invention provides a method for preparing acrylic acid and methyl acrylate. The method comprises passing the feed gas containing dimethoxymethane and carbon monoxide through a solid acid catalyst to generate acrylic acid and methyl acrylate with a high conversion rate and selectivity at a reaction temperature in a range from 180 to 400 and a reaction pressure in a range from 0.1 MPa to 15.0 MPa, the mass space velocity of dimethoxymethane in the feed gas is in a range from 0.05 $h^{-1}$ to 10.0 $h^{-1}$, and the volume percentage of dimethoxymethane in the feed gas is in a range from 0.1% to 95%.

17 Claims, 2 Drawing Sheets

(51) Int. Cl.
*B01J 29/40* (2006.01)
*B01J 29/65* (2006.01)
*B01J 29/70* (2006.01)
*C07C 67/37* (2006.01)
C07C 57/04 (2006.01)
C07C 69/54 (2006.01)

(52) U.S. Cl.
CPC ............ B01J 29/7019 (2013.01); C07C 67/37 (2013.01); *C07C 57/04* (2013.01); *C07C 69/54* (2013.01)

(58) Field of Classification Search
CPC ........ C07C 69/533; C07C 67/34; B01J 29/40; B01J 29/65; B01J 29/18; B01J 29/7019
See application file for complete search history.

METHOD FOR PREPARING ACRYLIC ACID AND METHYL ACRYLATE

This Application claims the benefit of priority of International Application No. PCT/CN2016/107284 filed on 25 Nov. 2016 the teachings of which are incorporated by reference herein in their entirety.

TECHNICAL FIELD

The present application relates to the field of solid acid catalysis, and in particular to a method for preparing acrylic acid and methyl acrylate using dimethoxymethane and carbon monoxide as raw materials for the reaction.

BACKGROUND

Acrylic acid is the simplest unsaturated carboxylic acid. Acrylic acid with a high purity has a characteristic pungent odor and is extremely corrosive. It is an important chemical raw material widely used in the synthesis of various chemicals and the production of resins. The acrylic acid and acrylate industries are an important part of the petrochemical production field in today's world.

The synthetic methods of acrylic acid mainly include: 1) chloroethanol method: chloroethanol and sodium cyanide are used as reaction raw materials to generate cyanoethanol in the presence of a basic catalyst at first, cyanoethanol is dehydrated in the presence of sulfuric acid to obtain acrylonitrile, and acrylonitrile is further subjected to hydrolysis or alcoholysis to obtain acrylic acid or acrylate; 2) cyanoethanol method: this method is developed from the chloroethanol method, except that the synthetic method of cyanoethanol is different, which is generated via a ring-opening reaction of ethylene oxide under the action of hydrocyanic acid; 3) high-pressure Reppe and modified Reppe method: the esterifying-grade acrylic acid is generated from acetylene, carbon monoxide and water under the action of a nickel salt or copper salt as catalyst, and is then subjected to an esterification reaction with different alcohols to generate acrylate; 4) ketene method: ethenone (prepared from acetone and acetic acid as raw materials) is reacted with anhydrous formaldehyde to generate β-propiolactone, which is then isomerized by contacting with hot phosphoric acid to generate acrylic acid; 5) formaldehyde-acetic acid method: an aldol condensation reaction of formaldehyde with acetic acid is carried out to directly generate acrylic acid; 6) acrylonitrile hydrolysis method; 7) ethylene method: an oxidative carbonylation reaction of ethylene with carbon monoxide and oxygen in the presence of a noble metal as catalyst is carried out to generate acrylic acid; 8) propylene direct oxidation method: it is further divided into one-step and two-step direct oxidation methods, wherein in the first step of the two-step oxidation method, propylene is oxidized to generate acrolein, and in the second step, acrolein is further oxidized to generate acrylic acid; 9) propane oxidation method: propane is used as a raw material, a metal oxide is used as a catalyst, and propane is directly oxidized to obtain acrylic acid; 10) ethylene oxide method: inserting carbon monoxide directly into ethylene oxide, that is, ethylene oxide is subject to a carbonylation reaction, to generate acrylic acid. Among the above 10 methods for producing acrylic acid, the chloroethanol method, the cyanoethanol method, the Reppe method and the ketene method have been gradually eliminated due to the expensive industrial costs caused by their low efficiency and high toxicity. As for the ethylene method, the propane method and the ethylene oxide method, the stability and selectivity of catalyst as well as the catalyst process are not yet mature, and there is currently no report on large-scale production. Only the propylene oxidation method has become the only method used in large-scale production of acrylic acid in the world today.

The propylene oxidation method was used at the earliest by the company UCC to build the first set of production device in 1969 in the United States, whereafter the Japanese company Nippon Shokubai Kagaku Kogyo (MCC) in 1970, the Japanese company Mitsubishi Chemical Corporation (NSKK) in 1973 and the American company Celanese in 1973 built successively production devices for producing acrylic acid by the propylene oxidation method. At present, the companies in the world owning the process technology for producing acrylic acid by oxidation of propylene all use the process of propylene two-step oxidation method.

Therefore, it is of important significance to develop a preparation method capable of generating acrylic acid and methyl acrylate from an inexpensive raw material with a high conversion rate and selectivity.

SUMMARY OF THE INVENTION

The object of the present application is to provide a method for preparing acrylic acid and methyl acrylate, which uses inexpensive dimethoxymethane (DMM) and carbon monoxide as reaction raw materials and a solid acid as a catalyst to generate acrylic acid and methyl acrylate with high selectivity.

In the method, a feed gas containing dimethoxymethane and carbon monoxide is passed through a reactor loaded with a molecular sieve catalyst to carry out a reaction, to generate acrylic acid as a main product and methyl acrylate, methyl acetate and acetic acid. After being separated, acetic acid, methyl acetate, acrylic acid and methyl acrylate are obtained, respectively.

According to some preferred embodiments of the present invention, the reaction is carried out at a reaction temperature in a range from 180 to 400 and a reaction pressure in a range from 0.1 MPa to 15.0 MPa, the mass space velocity of dimethoxymethane in the feed gas is in a range from 0.05 $h^{-1}$ to 10.0 $h^{-1}$, and the volume percentage of dimethoxymethane in the feed gas is in a range from 0.1% to 95%.

In the present application, the reaction process of reacting dimethoxymethane with carbon monoxide to generate acetic acid, methyl acetate, acrylic acid and methyl acrylate is as follows:

1) dimethoxymethane reacts with H-protonic acid of the solid acid (in the pores of molecular sieve) to generate a solid acid (molecular sieve) adsorption-activated methoxymethyl species, and to generate methanol simultaneously;

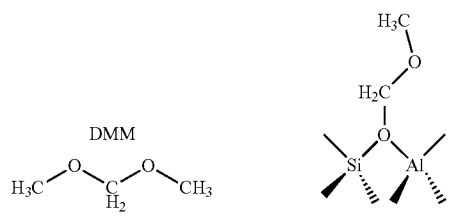

-continued

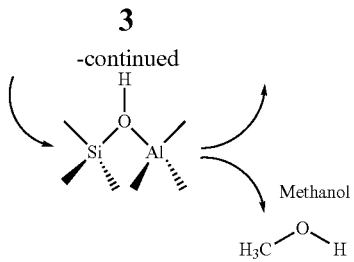

Methanol 2) the generated methanol reacts with an excess H-protonic acid of the solid acid (in the pores of molecular sieve) to generate a molecular sieve adsorption-activated methyl species and water;

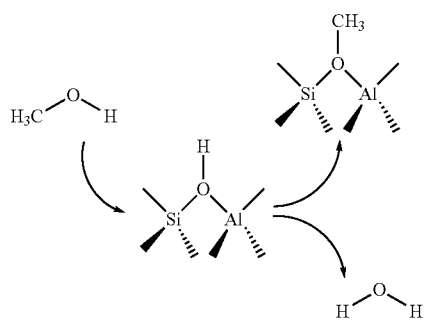

3) CO can be directly inserted into the solid acid (molecular sieve) adsorption-activated methoxymethyl species to generate a methoxyacetyl species;

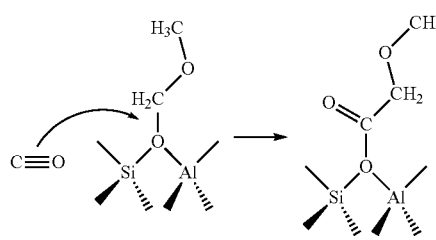

simultaneously,

4) CO can also be directly inserted into the solid acid (molecular sieve) adsorption-activated methyl species to generate an acetyl species;

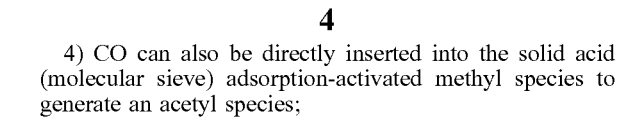

5) the solid acid (molecular sieve) adsorption-activated methoxymethyl species can undergo a self-disproportionation reaction with dimethoxymethane to generate a molecular sieve adsorption-activated dimethoxymethyl species and dimethyl ether;

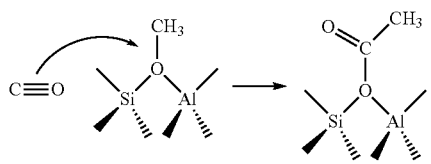

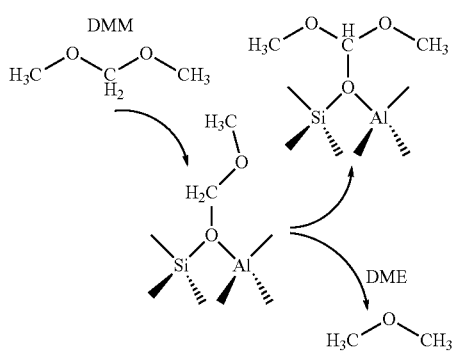

6) the solid acid (molecular sieve) adsorption-activated dimethoxymethyl species can generate dimethyl ether, formaldehyde and free solid acid (molecular sieve) acid sites under the action of water;

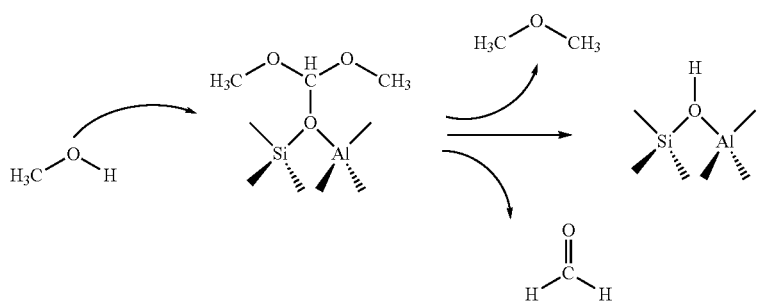

7) the solid acid (molecular sieve) adsorbed methoxyacetyl species can undergo a methyl-etherification reaction with dimethoxymethane to generate methyl methoxyacetate and the molecular sieve adsorbed methoxymethyl species; the solid acid (molecular sieve) adsorbed methoxyacetyl species can also undergo a methyl-etherification reaction with dimethyl ether to generate methyl methoxyacetate and a molecular sieve adsorbed methoxyl species; at the same time, the molecular sieve adsorbed methoxyacetyl species can also react with water to generate methoxyacetic acid and free solid acid (molecular sieve) acid sites (the latter two reactions have similar routes, without being drawn one by one);

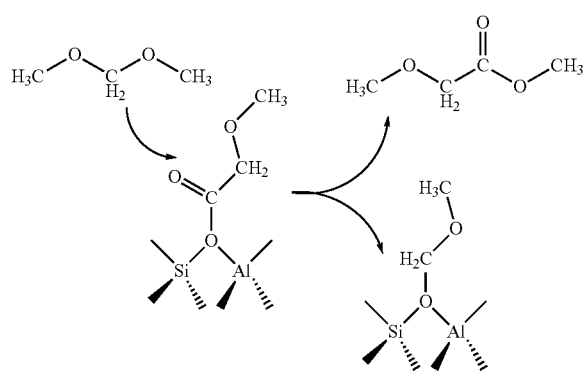

similarly, 8) the solid acid (molecular sieve) adsorption-activated methyl species can also undergo a methyl-etherification reaction with dimethyl ether to generate methyl acetate and the molecular sieve adsorbed methoxyl species; the solid acid (molecular sieve) adsorption-activated methyl species can also undergo a methyl-etherification reaction with dimethoxymethane to generate methyl acetate and the molecular sieve adsorbed methoxymethyl species; at the same time, the molecular sieve adsorbed acetyl species can also react with water or methanol to generate acetic acid and free molecular sieve acid sites or adsorbed methyl species (the latter two reactions have similar routes, without being drawn in entirety).

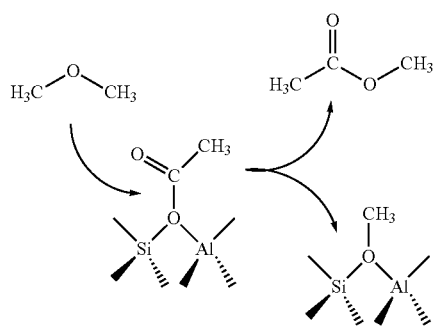

9) the generated acetic acid or methyl acetate can undergo an aldol condensation reaction with formaldehyde to generate acrylic acid and methyl acrylate.

According to the above reaction mechanisms, by means of the thermodynamic and kinetic factors, including controlling different temperature and pressure reaction conditions and different ratios of raw material composition, the products can be directionally controlled, such that they can be produced in accordance with the following equation. Under ideal conditions, in the products, the total selectivity based on carbon to acrylic acid is 60% and the total selectivity based on carbon to acetic acid is 40%, without formation of other by-products. If the selectivity to the product is calculated based on a single reaction raw material of dimethoxymethane, the selectivity based on carbon to acrylic acid is 50%, and the selectivity based on carbon to acetic acid is 50%.

$C_3H_8O_2$ (dimethoxymethane)+2CO=$C_3H_4O_2$
(acrylic acid)+$C_2H_4O_2$ (acetic acid)

In actual reactions, methyl acrylate and methyl acetate are partially generated in the product, due to the incomplete hydrolysis reaction of methyl acetate.

In the reaction product, the mass percentage content of acrylic acid is in a range from 0.1% to 70%, the mass percentage content of methyl acrylate is in a range from 0.1% to 30%, the mass percentage content of acetic acid is in a range from 0.1% to 60%, and the mass percentage content of methyl acetate is in a range from 0.1% to 40%.

The molecular sieve catalyst is any one or more selected from the group consisting of a ZSM-35 molecular sieve, a ZSM-5 molecular sieve, a MOR mordenite molecular sieve and a EMT molecular sieve.

The esters produced by the method can be further hydrolyzed to produce the corresponding carboxylic acids, including the hydrolysis of the methyl acrylate to produce the corresponding acrylic acid, and the hydrolysis of the methyl acetate to produce the corresponding acetic acid.

The esters and carboxylic acids produced by the method can be further hydrogenated to produce the corresponding alcohols, including the hydrogenation of the methyl acrylate and acrylic acid to produce the corresponding propanol, and the hydrogenation of the methyl acetate and acetic acid to produce the corresponding ethanol.

The atomic ratio of silicon to aluminum in the molecular sieve catalyst is preferably Si/Al=3 to 100.

The atomic ratio of silicon to aluminum in the ZSM-35 molecular sieve is preferably Si/Al=20 to 50.

The atomic ratio of silicon to aluminum in the ZSM-5 molecular sieve is preferably Si/Al=20 to 60.

The atomic ratio of silicon to aluminum in the mordenite is preferably Si/Al=10 to 30.

The atomic ratio of silicon to aluminum in the EMT zeolite is preferably Si/Al=5 to 20.

The molecular sieve can be obtained by heat treatment, hydrothermal treatment, inorganic acid treatment, organic acid treatment, $F^-$ treatment and chelate treatment or gas-solid phase dealuminization and silicon supplementation treatment.

The molecular sieves with different topologies comprise one or more selected from the group consisting of gallium, iron, copper and silver; the introduction methods may include in-situ synthesis, metal ion exchange or impregnation loading; and the metal content is in a range from 0.01 wt % to 10.0 wt % of the total weight of the catalyst, calculated by metal elementary substance.

Preferably, the metal content is in a range from 0.05 wt % to 1.0 wt % of the total weight of the catalyst.

The molecular sieve catalysts with different topologies contain a binder, the binder is any one or more selected from the group consisting of alumina, silica and magnesia, and the binder content is in a range from 0 wt % to 70 wt % of the total weight of the catalyst.

The reaction temperature is preferably in a range from 220° C. to 300° C.

The reaction pressure is preferably in a range from 5 MPa to 10 MPa.

The mass space velocity of dimethoxymethane in the raw material is preferably in a range from 0.3 h$^{-1}$ to 2.0 h$^{-1}$.

The volume percentage of dimethoxymethane in the raw material is preferably in a range from 0.5% to 30%.

The feed gas includes dimethoxymethane, carbon monoxide, hydrogen and an inactive gas, wherein the volume content of carbon monoxide is in a range from 50% to 95%, the volume content of hydrogen is in a range from 0% to 50%, and the volume content of the inactive gas is in a range from 0% to 50%. The inactive gas comprises any one or more selected from the group consisting of nitrogen, helium, argon, carbon dioxide, methane and ethane.

The reactor may be a fixed bed reactor, a fluidized bed reactor or a tank reactor.

The beneficial effects that can be achieved by the present application include:

1) According to the method provided by the present application, acrylic acid and methyl acrylate are synthesized with a high selectivity from inexpensive dimethoxymethane and carbon monoxide as reaction raw materials, and methyl acetate and acetic acid are by-produced.

2) According to the method provided by the present application, the products are acetic acid, methyl acetate, acrylic acid and methyl acrylate, and under normal pressure conditions, the four products are easily separated due to the great difference in the boiling point, so that acrylic acid and methyl acrylate of high added-values can be obtained with a low energy consumption and a low cost.

DETAILED DESCRIPTION OF THE EMBODIMENT

Figure 1:
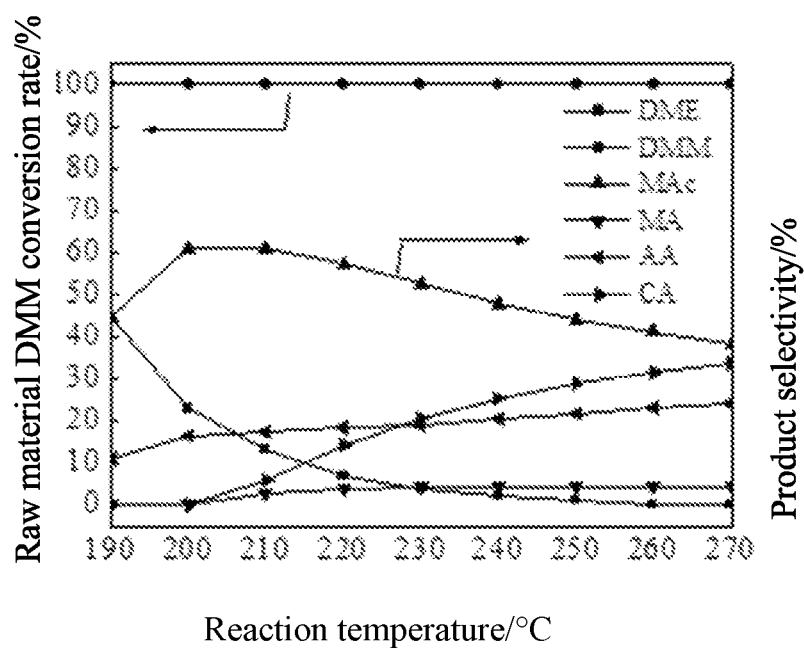
FIG. 1 is a graph showing the conversion rate of the raw material DMM and the selectivity to products with temperature at a total pressure of 5.0 MPa, a CO partial pressure of 2.5 MPa and a DMM partial pressure of $1.25 \times 10^{-2}$ MPa on the H-MOR molecular sieve in Example 1.

The present application will be further described below with reference to the examples. It is to be understood that the examples are for illustrative purposes only and are not intended to limit the scope of the present application.

The raw materials and catalysts in the examples of the present application are all commercially purchased, unless otherwise stated.

The analytical methods in the examples of the present application are as follows:

The raw materials and products were tested by Agilent's Agilent 7890A gas chromatograph using Agilent's FFAP capillary column.

According to an embodiment of the present application, a fixed bed reactor was used, the packing mass of catalyst was in a range from 0.5 g to 3.0 g, the reaction temperature was in a range from 180 to 350, and the reaction pressure was in a range from 0.1 MPa to 10 MPa. The raw material of dimethoxymethane was entered into the reactor by two ways of feeding:

In the first way, the saturated vapor of dimethoxymethane was carried by carbon monoxide at different water bath temperatures (0 to 50) to enter into the fixed bed reactor, to obtain feed gases of dimethoxymethane with different volume contents. The calculation method of the saturated vapor pressure of the raw material ethylene glycol dimethyl ether under different temperature conditions is as shown in Formula II:

$$\ln(p_1^*/p_2^*) = -\Delta_{vap}H_m \Delta VapH/8.3145 \times (1/T_1 - 1/T_2) \quad \text{Formula II}$$

wherein $p_1^*$ and $p_2^*$ represent the saturated vapor pressures of dimethoxymethane at different temperatures ($T_1$, $T_2$), respectively. It is known that dimethoxymethane has a molar enthalpy of vaporization $\Delta_{vap}H_m$ of 43.99 KJ/mol and a boiling point of 42.3, so that the saturated vapor pressure of dimethoxymethane at any temperature can be calculated. The amount of substance of the raw material dimethoxymethane entered into the reactor per unit time can be calculated by the saturated vapor pressure.

In the second way, the liquid raw material of dimethoxymethane was pumped directly into the fixed bed reactor by a constant flow pump at a flow rate in a range from 0.1 mL/min to 10 mL/min. In this way, the volume content of dimethoxymethane in the feed gas entering into the reactor to contact with the catalyst was in a range from 0.1% to 100%.

The conversion rate and selectivity in the examples of the present application are calculated as follows:

The conversion rate of dimethoxymethane=[(mole number of dimethoxymethane in the feed)−(mole number of dimethoxymethane in the discharge)]÷(mole number of dimethoxymethane in the feed)×(100%)

The selectivity to acrylic acid=⅔ (mole number of carbon in acrylic acid in the discharge)÷[(mole number of carbon in dimethoxymethane in the feed)−(mole number of carbon in dimethoxymethane in the discharge)]×(100%)

The selectivity to methyl acrylate=¾ (mole number of carbon in methyl acrylate in the discharge)÷[(mole number of carbon in dimethoxymethane in the feed)−(mole number of carbon in dimethoxymethane in the discharge)]×(100%)

The selectivity to acetic acid=½ (mole number of carbon in acetic acid in the discharge)÷[(mole number of carbon in dimethoxymethane in the feed)−(mole number of carbon in dimethoxymethane in the discharge)]×(100%)

The selectivity to methyl acetate=⅔ (mole number of carbon in methyl acetate in the discharge)÷[(mole number of carbon in dimethoxymethane in the feed)−(mole number of carbon in dimethoxymethane in the discharge)]×(100%)

Preparation of Catalyst

H-Mordenite Catalyst 100 g of calcined Na-mordenite zeolite molecular sieves, with an aluminum atomic molar ratio of 5, 6.5, 25 and 50 respectively, were each exchanged three times with 0.5 mol/L ammonium nitrate (2 hours for each time), washed with deionized water, dried, calcined at 550 for 4 hours, and extruded to prepare catalysts of 20-40 mesh.

Ga-Mordenite Catalyst 100 g of calcined gallium-containing Na-mordenite (silicon-aluminum atomic molar ratio of 5) zeolite molecular sieve was exchanged three times with 0.5 mol/L ammonium nitrate (2 hours for each time), washed with deionized water, dried, calcined at 550 for 4 hours, and extruded to prepare a catalyst of 20-40 mesh.

Fe-Mordenite Catalyst 100 g of calcined iron-containing Na-mordenite (silicon-aluminum atomic molar ratio of 6.5) zeolite molecular sieve was exchanged three times with 0.5 mol/L ammonium nitrate (2 hours for each time), washed with deionized water, dried, calcined at 550 for 4 hours, and extruded to prepare a catalyst of 20-40 mesh.

Loaded Type M/H-Mordenite Catalyst

The loaded type catalyst was prepared by the equal volume impregnation method. 4.32 g of $Fe(NO_3)_3$, 4.32 g of $Cu(NO_3)_2 \cdot 3H_2O$ and 3.04 g of $AgNO_3 \cdot 3H_2O$ were each dissolved in 18 ml of deionized water to prepare the corresponding aqueous nitrate solutions. 20 g of H-mordenite zeolite molecular sieve with a silicon-aluminum ratio of 25 was placed in the aqueous ferric nitrate solution, and stood for 24 hours. The obtained sample was dried in an oven at 120 for 12 hours. After drying, the sample was placed in a muffle furnace, heated to 550 at a heating rate of 2/min and then calcined for 4 hours to prepare a catalyst.

Ion exchange type M-mordenite catalyst g of H-mordenite and 300 ml of an aqueous ferric nitrate solution (0.15 mol) were placed in a flask, and stirred under cooling and refluxing at 80 for 2 hours, with the solid-liquid ratio being 1:15. The resultant was separated by filtration, washed with deionized water, treated by repeating the above steps twice, and dried at 120 for 12 hours. After drying, the sample was placed in a muffle furnace, heated to 550 at a heating rate of 2/min, and calcined for 4 hours to obtain a catalyst.

Molding of H-Mordenite Catalyst 80 g of Na-mordenite with a silicon-aluminum atomic molar ratio of 6.5, g of pseudo-boehmite and 10% dilute nitric acid were mixed homogeneously and extruded for molding, then calcined, exchanged with 0.5 mol/L ammonium nitrate for three times (2 hours for each time), washed with deionized water, dried, and calcined at 550 for 4 hours to obtain a catalyst.

80 g of Na-mordenite with a silicon-aluminum atomic molar ratio of 4, 20 g of magnesia and 10% dilute nitric acid were mixed homogeneously and extruded for molding, then calcined, exchanged with 0.5 mol/L ammonium nitrate for three times (2 hours for each time), washed with deionized water, dried, and calcined at 550 for 4 hours to obtain a catalyst.

80 g of Na-mordenite with a silicon-aluminum atomic molar ratio of 4, 50 g of silica sol and 10% dilute nitric acid were mixed homogeneously and extruded for molding, then calcined, exchanged with 0.5 mol/L ammonium nitrate for three times (2 hours for each time), washed with deionized water, dried, and calcined at 550 for 4 hours to obtain a catalyst.

H-ZSM-35 Catalyst 100 g of calcined Na-ZSM-35 molecular sieves, with a silicon-aluminum atomic molar ratio of 20, 35 and 50 respectively, were each exchanged with 0.5 mol/L ammonium nitrate for three times (2 hours for each time), washed with deionized water, dried, calcined at 550 for 4 hours, and extruded to prepare catalysts of 20-40 mesh.

H-ZSM-5 Catalyst 100 g of calcined Na-ZSM-5 molecular sieves, with a silicon-aluminum atomic molar ratio of 20, 40 and 60 respectively, were each exchanged with 0.5 mol/L ammonium nitrate for three times (2 hours for each time), washed with deionized water, dried, calcined at 550 for 4 hours, and extruded to prepare catalysts of 20-40 mesh.

H-EMT Catalyst

The synthetic H-EMT molecular sieves, with a silicon-aluminum atomic molar ratio of 5, 10 and 20 respectively, were each extruded to prepare catalysts of 20-40 mesh.

Example 1

The H-MOR molecular sieve with a silicon-aluminum ratio Si/Al=6.5 was tableted under a pressure of 40 MPa, and crushed to 20-40 mesh to obtain a catalyst. 0.4 g of the catalyst was packed into a fixed bed reactor for pretreatment. The pretreatment conditions for the catalyst were as follows: the $N_2$ flow rate was 30 mL/min, and the temperature was raised from 25° C. to 500 for 150 min and maintained at 500° C. for 180 min The reaction gas was consisted of three gas streams, and a total flow rate of 100 mL/min was ensured. The raw material of dimethoxymethane was carried into the reactor by CO at a flow rate of 10 ml/min under a water bath temperature of 30° C.; the flow rates of another stream of pure CO were 0 mL/min, 10 mL/min, 40 mL/min and 90 mL/min respectively; the flow rates of the third stream of $N_2$ were 90 mL/min, 80 mL/min, 50 mL/min and 0 mL/min respectively. The total pressure of reaction was 5.0 MPa. The reaction temperature was maintained at 190° C. for 300 min, then increased to 200° C. in 5 min, maintained at 200° C. for another 300 min, and then increased to 210° C. in 5 min. According to the above rule, the temperature was maintained for 300 min for each increase by 10° C., until it was increased to 270° C. and then maintained for 300 min. The raw material of DMM had a partial pressure of about $1.25 \times 10^{-2}$ MPa (0.0125 atm), and the total CO partial pressures were approximately 0.5, 1.0, 2.5 and 5.0 MPa.

When the partial pressure of CO is 2.5 MPa, the graph of the conversion rate of the raw material DMM and the selectivity to the products with temperature is shown in FIG. 1. As can be seen from FIG. 1, on the H-MOR (Si/Al=6.5) catalyst, when the reaction temperature is higher than 190, the conversion rate of the raw material DMM is close to 100%. Five products are substantially generated, namely dimethyl ether (DME), methyl acetate (MAc), acetic acid (AA), methyl acrylate (MA) and acrylic acid (CA). The selectivities to the products of dimethyl ether and methyl acetate decrease gradually with increase in the reaction temperature. When the reaction temperature reaches to 240° C., almost no dimethyl ether is generated; when the reaction temperature reaches to 270° C., the selectivity to methyl acetate is reduced to 40%. When the reaction temperature is higher than 200, a small amount of acrylic acid is generated in the products, the selectivity of which increases as the reaction temperature increases, and the highest selectivity reaches to 35% as the reaction temperature reaches to 270. The product of methyl acrylate is accompanied by the generation of acrylic acid, and its selectivity is stabilized constantly at around 3%. The selectivity to the product of acetic acid also increases gradually as the reaction temperature increases, but the change is not obvious, and the selectivity increases from 10% at the initial 190° C. to 23% at 270° C.

Table 1 shows the distribution of product as a function of the reaction temperature at a DMM partial pressure of $1.25 \times 10^{-2}$ MPa (0.0125 atm) and CO partial pressures of 0.5 MPa, 1.0 MPa and 5.0 MPa respectively. It can be known from Table 1 that under all conditions, the conversion rate of the raw material DMM is close to 100%, and the selectivity to the product of acrylic acid is higher at the same reaction temperature as the CO partial pressure increases. When the partial pressure of CO is 5.0 MPa, the selectivity to acrylic acid reaches to 37% at 240° C. The partial pressure of CO has little effect on the selectivity to acetic acid, and the selectivity to acetic acid is basically stabilized at 20-25%.

Example 2

The H-MOR molecular sieve with a silicon-aluminum ratio Si/Al=6.5 was tableted under a pressure of 40 MPa, and crushed to 20-40 mesh to obtain a catalyst. 0.4 g of the catalyst was packed into a fixed bed reactor for pretreatment. The pretreatment conditions for the catalyst were as follows: the $N_2$ flow rate was 30 mL/min, and the temperature was raised from 25° C. to 500 for 150 min and maintained at 500° C. for 180 min The reaction gas was consisted of two gas streams, and a total flow rate of 100 mL/min was ensured. The raw material of dimethoxymethane was carried into the reactor by CO at flow rates of 2 mL/min, 5 mL/min, 10 mL/min, 25 mL/min, 50 mL/min and 100 mL/min under water bath temperatures of 0° C. and 30° C.; the flow rates of another stream of pure CO were 98 mL/min, 95 mL/min, 90 mL/min, 75 mL/min, 50 mL/min and 0 mL/min respectively. The total reaction pressure was 5.0 MPa. The reaction temperature was maintained at 190° C. for 300 min, then increased to 200° C. in 5 min, maintained at 200° C. for another 300 min, and then increased to 210° C. in 5 min. According to the above rule, the temperature was maintained for 300 min for each increase by 10° C., until it was increased to 270° C. and then maintained for 300 min. The partial pressures of the raw material DMM were $0.21 \times 10^{-2}$ MPa (0.0021 atm), $0.416 \times 10^{-2}$ MPa (0.00416 atm), $1.25 \times 10^{-2}$ MPa (0.0125 atm), $3.125 \times 10^{-2}$ MPa (0.3125 atm), $6.25 \times 10^{-2}$ MPa (0.625 atm) and $12.5 \times 10^{-2}$ MPa (0.125 atm) respectively. Among them, the reaction data at the partial pressure of $1.25 \times 10^{-2}$ MPa (0.0125 atm) for the raw material DMM is shown in FIG. 1, and other reaction data is shown in Table 2. When the partial pressure of DMM is lower than $3.125 \times 10^{-2}$ MPa, the conversion rate of DMM is close to 100% under any reaction temperature. When the partial pressure of DMM is higher than $3.125 \times 10^{-2}$ MPa, the conversion rate of DMM increases gradually as the reaction temperature increases. When the partial pressure of DMM is $0.21 \times 10^{-2}$ MPa and the reaction temperature is 190, the products are methyl acetate and acetic acid, with selectivities of 56% and 44%, respectively. As the reaction temperature increases, the selectivities to methyl acetate and acetic acid are gradually reduced, accompanied by the generation of acrylic acid and methyl acrylate, and the selectivity to acrylic acid increases as the reaction temperature increases. When the reaction temperature is higher than or equal to 250, the selectivity to acrylic acid reaches to a maximum of 48%, and remains substantially unchanged as the reaction temperature increases thereafter. When the reaction temperature is higher than 250, with the partial pressure of DMM being increased to $0.416 \times 10^{-2}$ MPa, the selectivity to acrylic acid is stabilized at around 40%. As the partial pressure of DMM increases, the selectivity to acrylic acid gradually decreases under the same reaction temperature conditions. When the partial pressure of DMM is $12.5 \times 10^{-2}$ MPa and the reaction temperature is 270, the selectivity to acrylic acid is only 4%.

Example 3

Figure 2:
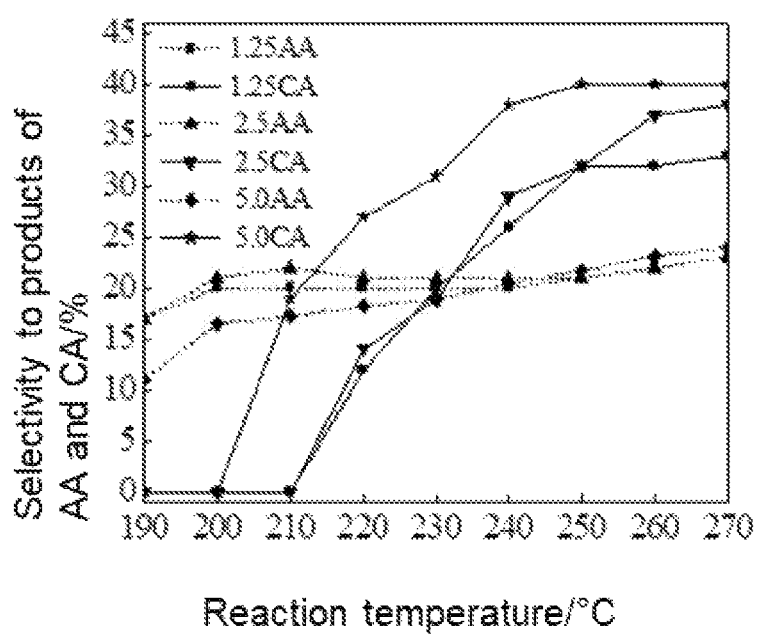
FIG. 2 is a graph showing the relationship between the total reaction pressure and the selectivity to the products of acetic acid and acrylic acid as a function of reaction temperature on the H-MOR molecular sieve in Example 3.

The H-MOR molecular sieve with a silicon-aluminum ratio Si/Al=6.5 was tableted under a pressure of 40 MPa, and crushed to 20-40 mesh to obtain a catalyst. 0.4 g of the catalyst was packed into a fixed bed reactor for pretreatment. The pretreatment conditions for the catalyst were as follows: the $N_2$ flow rate was 30 mL/min, and the temperature was raised from 25° C. to 500 for 150 min and maintained at 500° C. for 180 min The reaction gas was consisted of two gas streams, and a total flow rate of 100 mL/min was ensured. The molar ratio of CO to DMM was maintained at 400:1 (that is, to ensure the peak area of the raw material DMM in the chromatogram was kept constant) by adjusting the water bath temperature of the raw material DMM and the flow rate of the CO carrier gas. The total reaction pressures were adjusted to be 1.25 MPa, 2.50 MPa and 5.0 MPa, respectively. The reaction temperature was maintained at 190° C. for 90 min, then increased to 200° C. in 5 min, maintained at 200° C. for another 90 min, and then increased to 210° C. in 5 min According to the above rule, the temperature was maintained for 90 min for each increase by 10° C., until it was increased to 270° C. and then maintained for 90 min. The graph of the conversion rate of the raw material DMM and the selectivity to the products of acetic acid and acrylic acid as a function of temperature is shown in FIG. 2. In the case that the ratio of CO to DMM is kept constant, the selectivity to acetic acid remains basically unchanged as the total reaction pressure is increased gradually. However, when the total reaction pressure is 5.0 MPa, the selectivity to the product of acrylic acid is significantly higher than the selectivities to acrylic acid at the total pressures of 1.25 MPa and 2.50 MPa at the same temperature. This is because the aldol condensation reaction is a reaction in which the number of molecules is reduced, and an increased reaction pressure is favorable for the reaction to proceed in the positive direction.

Example 4

A fixed bed reactor was used, and the packing mass of catalyst was in a range from 0.1 g to 5.0 g. The molecular sieves having different silicon-aluminum ratios with topologies of MWW, FER, MFI, MOR, FAU and BEA, including H-MCM-22, H-ZSM-35, H-ZSM-5, H-MOR, H-Y, H-Beta and the metal modified Ga-mordenite, Fe-mordenite, Cu-mordenite as well as the molded catalysts of H-mordenite-$Al_2O_3$, H-mordenite-$SiO_2$ and H-mordenite-MgO, were tableted at a pressure of 40 MPa, and crushed to 20-40 mesh to obtain catalysts. The reaction results of acidic resin catalysts and solid sulfonic acid catalysts at the conditions of a reaction temperature in a range from 180 to 350, a reaction pressure in a range from 0.1 MPa to 10 MPa, a mass space velocity of raw material DMM in a range from 0.05 $h^{-1}$ to 10 $h^{-1}$ and a volume percentage in a range from 0.1% to 100% are shown in Table 3.

TABLE 1

Reaction results of dimethoxymethane under different temperatures and CO partial pressures

| Reaction temperature/ | CO partial pressure/MPa | Conversion rate/% Dimethoxymethane | Selectivity to product/% | | | | |
|---|---|---|---|---|---|---|---|
| | | | Dimethyl ether | Methyl acetate | Methyl acrylate | Acetic acid | acrylic acid |
| 190 | 0.5 | 100 | 90 | 10 | 0 | 0 | 0 |
| | 1.0 | 100 | 75 | 25 | 0 | 0 | 0 |
| | 5.0 | 100 | 14 | 70 | 0 | 16 | 0 |
| 200 | 0.5 | 100 | 75 | 25 | 0 | 0 | 0 |
| | 1.0 | 100 | 60 | 35 | 0 | 5 | 0 |
| | 5.0 | 100 | 9 | 64 | 2 | 16 | 9 |
| 210 | 0.5 | 100 | 40 | 56 | 0 | 4 | 0 |
| | 1.0 | 100 | 28 | 59 | 1 | 9 | 3 |
| | 5.0 | 100 | 3 | 62 | 3 | 16 | 16 |
| 220 | 0.5 | 100 | 16 | 72 | 2 | 10 | 0 |
| | 1.0 | 100 | 10 | 63 | 3 | 12 | 12 |
| | 5.0 | 100 | 2 | 50 | 3 | 17 | 28 |
| 230 | 0.5 | 100 | 6 | 64 | 6 | 15 | 9 |
| | 1.0 | 100 | 4 | 55 | 5 | 19 | 17 |
| | 5.0 | 100 | 1 | 42 | 3 | 20 | 34 |
| 240 | 0.5 | 100 | 2 | 52 | 9 | 19 | 18 |
| | 1.0 | 100 | 1 | 50 | 7 | 21 | 21 |
| | 5.0 | 100 | 0 | 37 | 4 | 22 | 37 |
| 250 | 0.5 | 100 | 1 | 42 | 9 | 22 | 26 |
| | 1.0 | 100 | 0 | 41 | 7 | 23 | 29 |
| | 5.0 | 100 | 0 | 34 | 4 | 23 | 39 |
| 260 | 0.5 | 100 | 0 | 36 | 9 | 23 | 32 |
| | 1.0 | 100 | 0 | 37 | 7 | 23 | 34 |
| | 5.0 | 100 | 0 | 33 | 4 | 24 | 39 |
| 270 | 0.5 | 100 | 0 | 34 | 9 | 24 | 33 |
| | 1.0 | 100 | 0 | 36 | 7 | 24 | 35 |
| | 5.0 | 100 | 0 | 32 | 4 | 25 | 39 |

TABLE 2

Reaction results under different temperatures and partial pressures of dimethoxymethane

| Reaction temperature/ | Partial pressure of DMM/$10^{-2}$ MPa | Conversion rate/% Dimethoxymethane | Selectivity to product/% | | | | |
|---|---|---|---|---|---|---|---|
| | | | Dimethyl ether | Methyl acetate | Methyl acrylate | Acetic acid | acrylic acid |
| 190 | 0.210 | 100 | 0 | 56 | 0 | 44 | 0 |
| | 0.416 | 100 | 0 | 60 | 0 | 40 | 0 |
| | 3.125 | 100 | 67 | 24 | 0 | 9 | 0 |
| | 6.250 | 57 | 81 | 17 | 0 | 2 | 0 |
| | 12.500 | 36 | 76 | 9 | 0 | 0 | 0 |
| 200 | 0.210 | 100 | 0 | 50 | 0 | 50 | 0 |
| | 0.416 | 100 | 0 | 62 | 0 | 48 | 0 |
| | 3.125 | 100 | 18 | 68 | 0 | 12 | 2 |
| | 6.250 | 61 | 66 | 32 | 0 | 2 | 0 |
| | 12.500 | 49 | 74 | 16 | 0 | 0 | 0 |
| 210 | 0.210 | 100 | 0 | 46 | 0 | 54 | 0 |
| | 0.416 | 100 | 0 | 60 | 0 | 40 | 0 |
| | 3.125 | 100 | 8 | 64 | 2 | 14 | 12 |
| | 6.250 | 78 | 57 | 37 | 0 | 6 | 0 |
| | 12.500 | 64 | 69 | 21 | 0 | 2 | 0 |
| 220 | 0.210 | 100 | 0 | 33 | 0 | 38 | 29 |
| | 0.416 | 100 | 0 | 40 | 0 | 36 | 24 |
| | 3.125 | 100 | 2 | 59 | 2 | 17 | 20 |
| | 6.250 | 89 | 48 | 41 | 1 | 8 | 2 |
| | 12.500 | 79 | 63 | 29 | 0 | 1 | 0 |
| 230 | 0.210 | 100 | 0 | 27 | 0 | 34 | 39 |
| | 0.416 | 100 | 0 | 41 | 2 | 30 | 27 |
| | 3.125 | 100 | 0 | 52 | 3 | 20 | 25 |
| | 6.250 | 93 | 41 | 46 | 2 | 9 | 2 |
| | 12.500 | 85 | 54 | 33 | 2 | 4 | 2 |
| 240 | 0.210 | 100 | 0 | 23 | 0 | 34 | 43 |
| | 0.416 | 100 | 0 | 33 | 2 | 32 | 33 |
| | 3.125 | 100 | 0 | 44 | 3 | 21 | 32 |
| | 6.250 | 94 | 30 | 50 | 2 | 11 | 7 |
| | 12.500 | 89 | 49 | 40 | 3 | 4 | 3 |

TABLE 2-continued

Reaction results under different temperatures and partial pressures of dimethoxymethane

| Reaction temperature/ | Partial pressure of DMM/$10^{-2}$ MPa | Conversion rate/% Dimethoxymethane | Selectivity to product/% | | | | |
|---|---|---|---|---|---|---|---|
| | | | Dimethyl ether | Methyl acetate | Methyl acrylate | Acetic acid | acrylic acid |
| 250 | 0.210 | 100 | 0 | 17 | 0 | 35 | 48 |
| | 0.416 | 100 | 0 | 29 | 2 | 33 | 36 |
| | 3.125 | 100 | 0 | 42 | 3 | 20 | 35 |
| | 6.250 | 94 | 24 | 51 | 3 | 12 | 10 |
| | 12.500 | 92 | 45 | 40 | 3 | 4 | 3 |
| 260 | 0.210 | 100 | 0 | 16 | 0 | 36 | 48 |
| | 0.416 | 100 | 0 | 23 | 2 | 35 | 39 |
| | 3.125 | 100 | 0 | 40 | 3 | 21 | 36 |
| | 6.250 | 94 | 20 | 51 | 3 | 13 | 13 |
| | 12.500 | 92 | 43 | 42 | 3 | 5 | 4 |
| 270 | 0.210 | 100 | 0 | 14 | 0 | 38 | 48 |
| | 0.416 | 100 | 0 | 22 | 2 | 37 | 39 |
| | 3.125 | 100 | 0 | 39 | 3 | 21 | 37 |
| | 6.250 | 94 | 18 | 52 | 3 | 13 | 14 |
| | 12.500 | 92 | 43 | 42 | 3 | 5 | 4 |

TABLE 3

Catalytic reaction results of dimethoxymethane on surfaces and in pores of different solid acid catalysts

| | | | Reaction condition | | | | Reaction result | |
|---|---|---|---|---|---|---|---|---|
| No. | Catalyst Type | Si/Al | Reaction temperature ( ) | Reaction pressure (MPa) | Mass space velocity of dimethoxy-methane ($h^{-1}$) | Volume content of dimethoxy-methane (%) | Conversion rate of dimethoxy-methane (%) | Selectivity to acrylic acid (%) |
| 1 | H-mordenite | 5 | 250 | 5 | 0.25 | 0.1 | 100 | 50 |
| 2 | H-mordenite | 6.5 | 350 | 8 | 1.00 | 1.0 | 100 | 50 |
| 3 | H-mordenite | 25 | 240 | 10 | 0.50 | 0.5 | 100 | 40 |
| 4 | H-mordenite | 50 | 240 | 10 | 0.50 | 0.5 | 100 | 40 |
| 6 | H-ZSM-35 | 5 | 270 | 10 | 0.25 | 1.0 | 100 | 9 |
| 7 | H-ZSM-35 | 25 | 280 | 10 | 0.25 | 0.25 | 100 | 15 |
| 8 | H-ZSM-35 | 50 | 290 | 10 | 0.25 | 0.5 | 100 | 16 |
| 9 | H-ZSM-35 | 100 | 300 | 10 | 0.25 | 0.5 | 100 | 20 |
| 10 | H-ZSM-5 | 25 | 260 | 5 | 0.5 | 0.1 | 100 | 4 |
| 11 | H-ZSM-5 | 50 | 260 | 5 | 0.5 | 0.1 | 100 | 4 |
| 12 | Benzenesulfonic acid | — | 170 | 10 | 0.1 | 0.5 | 38 | 28 |
| 13 | p-Methylbenzene sulfonic acid | — | 170 | 10 | 0.1 | 0.5 | 46 | 31 |
| 14 | Perfluorinated sulfonic acid resin | — | 170 | 10 | 0.1 | 0.5 | 80 | 32 |
| 15 | Ga-mordenite | 5 | 250 | 3 | 1.00 | 1.0 | 100 | 36 |
| 16 | Fe-mordenite | 6.5 | 250 | 3 | 1.00 | 1.0 | 100 | 50 |
| 17 | Cu-mordenite | 25 | 250 | 3 | 1.00 | 1.0 | 100 | 43 |
| 18 | H-mordenite-$Al_2O_3$ | 6.5 | 240 | 5 | 3.0 | 5.0 | 86 | 50 |
| 19 | H-mordenite-$SiO_2$ | 6.5 | 240 | 5 | 3.0 | 5.0 | 88 | 50 |
| 20 | H-mordenite-MgO | 6.5 | 240 | 5 | 3.0 | 5.0 | 96 | 50 |

The above are only a few embodiments of the present application, and are not intended to limit the present application in any form. Although the present application is disclosed by the preferred embodiments as above, they are however not used to limit the present application. A slight change or modification utilizing the technical content disclosed above made by the person skilled in art, without departing from the technical solution of the present application, is equivalent to the equivalent embodiment, and falls within the scope of the technical solution.

What is claimed is:

1. A method, for preparing acrylic acid and methyl acrylate, the method comprising passing a feed gas containing dimethoxymethane and carbon monoxide through a reactor loaded with a molecular sieve catalyst to carry out a reaction, to generate acrylic acid and methyl acrylate, methyl acetate and acetic acid;
   wherein the esters produced by the method are further hydrolyzed to produce the corresponding carboxylic acids, including the hydrolysis of the methyl acrylate to produce the corresponding acrylic acid, and the hydrolysis of the methyl acetate to produce the corresponding acetic acid.

2. The method according to claim 1, wherein the esters and carboxylic acids produced by the method are further hydrogenated to produce the corresponding alcohols, including the hydrogenation of the methyl acrylate and acrylic acid to produce the corresponding propanol, and the hydrogenation of the methyl acetate and acetic acid to produce the corresponding ethanol.

3. The method according to claim 1, wherein the molecular sieve catalyst contains a binder, the binder is any one or more selected from the group consisting of alumina, silica and magnesia, and the binder content is in a range from 0 wt % to 70 wt % of the total weight of the catalyst.

4. The method according to claim 1, wherein the feed gas includes hydrogen and an inactive gas in addition to dimethoxymethane and carbon monoxide, wherein the volume content of carbon monoxide is in a range from 50% to 95%, the volume content of hydrogen is in a range from 0% to 50%, and the volume content of the inactive gas is in a range from 0% to 50%; and the inactive gas includes any one or more selected from the group consisting of nitrogen, helium, argon, carbon dioxide, methane and ethane.

5. The method according to claim 1, wherein the reactor is a fixed bed reactor, a fluidized bed reactor or a tank reactor.

6. The method according to claim 1, wherein the reaction is carried out at a reaction temperature in a range from 180° C. to 400° C. and a reaction pressure in a range from 0.1 MPa to 15.0 MPa, the mass space velocity of dimethoxymethane in the feed gas is in a range from 0.05 $h^{-1}$ to 10.0 $h^{-1}$, and the volume percentage of dimethoxymethane in the feed gas is in a range from 0.1% to 95%.

7. The method according to claim 1, wherein the molecular sieve catalyst is any one or more selected from the group consisting of a ZSM-35 molecular sieve, a ZSM-5 molecular sieve, a MOR mordenite molecular sieve and a EMT molecular sieve.

8. The method according to claim 7, wherein the atomic ratio of silicon to aluminum in the molecular sieve catalyst is Si/Al=3 to 100.

9. The method according to claim 7, wherein
the atomic ratio of silicon to aluminum in the ZSM-35 molecular sieve is Si/Al=20 to 50;
the atomic ratio of silicon to aluminum in the ZSM-5 molecular sieve is Si/Al=20 to 60;
the atomic ratio of silicon to aluminum in the mordenite is Si/Al=10 to 30; and
the atomic ratio of silicon to aluminum in the EMT zeolite is Si/Al=5 to 20.

10. The method according to claim 7, wherein the molecular sieve catalyst is obtained by heat treatment, hydrothermal treatment, inorganic acid treatment, organic acid treatment, F treatment, chelate treatment, or gas-solid phase dealuminization and silicon supplementation treatment.

11. The method according to claim 7, wherein the molecular sieve catalyst comprises one or more selected from the group consisting of gallium, iron, copper and silver; introduction methods comprise in-situ synthesis, metal ion exchange or impregnation loading; and the metal content is in a range from 0.01 wt % to 10.0 wt % of the total weight of the catalyst, calculated by metal elementary substance.

12. The method according to claim 11, wherein the metal content is in a range from 0.05 wt % to 1.0 wt % of the total weight of the catalyst.

13. The method according to claim 6, wherein the reaction temperature is in a range from 220° C. to 300° C.

14. The method according to claim 6, wherein the reaction pressure is in a range from 5 MPa to 10 MPa.

15. The method according to claim 6, wherein the mass space velocity of dimethoxymethane in the feed gas is in a range from 0.3 $h^{-1}$ to 2.0 $h^{-1}$.

16. The method according to claim 6, wherein the volume percentage of dimethoxymethane in the feed gas is in a range from 0.5% to 30%.

17. The method according to claim 8, wherein
the atomic ratio of silicon to aluminum in the ZSM-35 molecular sieve is Si/Al=20 to 50;
the atomic ratio of silicon to aluminum in the ZSM-5 molecular sieve is Si/Al=20 to 60;
the atomic ratio of silicon to aluminum in the mordenite is Si/Al=10 to 30; and
the atomic ratio of silicon to aluminum in the EMT zeolite is Si/Al=5 to 20.

\* \* \* \* \*